US008501814B2

(12) United States Patent
Ratilainen et al.

(10) Patent No.: US 8,501,814 B2
(45) Date of Patent: Aug. 6, 2013

(54) SELECTIVE ANDROGEN RECEPTOR MODULATORS

(75) Inventors: Jari Ratilainen, Kulho (FI); Olli Törmäkangas, Turku (FI); Arja Karjalainen, Espoo (FI); Paavo Huhtala, Espoo (FI)

(73) Assignee: Orion Corporation, Espoo (FI)

( * ) Notice: Subject to any disclaimer, the term of this patent is extended or adjusted under 35 U.S.C. 154(b) by 581 days.

(21) Appl. No.: 12/280,026

(22) PCT Filed: Mar. 2, 2007

(86) PCT No.: PCT/FI2007/000055
§ 371 (c)(1),
(2), (4) Date: Sep. 4, 2008

(87) PCT Pub. No.: WO2007/099200
PCT Pub. Date: Sep. 7, 2007

(65) Prior Publication Data
US 2009/0054525 A1    Feb. 26, 2009

Related U.S. Application Data

(60) Provisional application No. 60/778,417, filed on Mar. 3, 2006.

(51) Int. Cl.
*A61K 31/167*    (2006.01)
*C07C 255/51*    (2006.01)
*C07C 233/01*    (2006.01)

(52) U.S. Cl.
USPC .............. 514/619; 558/414; 564/167

(58) Field of Classification Search
USPC .............. 514/619; 558/414; 564/167
See application file for complete search history.

(56) References Cited

U.S. PATENT DOCUMENTS 7,390,923 B2 *    6/2008    Ratilainen et al. ............ 564/138
7,855,229 B2 *    12/2010    Dalton et al. ................ 514/522

FOREIGN PATENT DOCUMENTS

WO    WO 2005/000794    1/2005
WO    WO 2005/000794 A1 *    1/2005

OTHER PUBLICATIONS

International Search Report dated May 16, 2007 for International Application No. PCT/FI2007/000055.

* cited by examiner

*Primary Examiner* — Joseph Kosack
(74) *Attorney, Agent, or Firm* — Finnegan, Henderson, Farabow, Garrett & Dunner, LLP

(57) ABSTRACT

A compound of formula (I), an isomer, metabolite, or a pharmaceutically acceptable salt or ester thereof is disclosed. Compounds of the invention possess utility as a tissue-selective androgen receptor modulators (SARM) and are useful in hormonal therapy, e.g. in the treatment or prevention of hypogonadism, muscle wasting, osteoporosis, benign prostate hyperplasia, obesity associated with a metabolic syndrome, male and female sexual dysfunction and reduced libido, and androgen decline in aging male or female.

6 Claims, No Drawings

SELECTIVE ANDROGEN RECEPTOR MODULATORS

This application is a national stage filing under 35 U.S.C. §371 of International Application No. PCT/FI2007/000055, filed on Mar. 2, 2007, which claims the benefit of priority of U.S. Provisional Application No. 60/778,417 filed on Mar. 3, 2006. The contents of each application are incorporated herein by reference.

TECHNICAL FIELD

The present invention relates to therapeutically active compounds that are useful in the treatment of androgen receptor (AR) dependent conditions. In particular, the invention discloses novel compounds having utility as tissue-selective androgen receptor modulators (SARM). The compounds of the invention, which possess AR agonist activity, are useful in hormonal therapy, especially in treatment or prevention of AR dependent conditions such as hypogonadism, muscle wasting, osteoporosis, benign prostate hyperplasia, obesity associated with a metabolic syndrome, male and female sexual dysfunction and reduced libido, and androgen decline in aging male or female.

BACKGROUND OF THE INVENTION

Non-steroidal propionanilides having AR modulating activity have been described e.g. in patent publications EP 100172, EP 253503, WO 98/53826 and WO 02/16310. The design of propionanilide structured AR modulators has concentrated on compounds where the anilide ring is substituted by two electron-withdrawing substituents, such as trifluoromethyl and nitro, since such substitution has been reported to enhance the androgen receptor binding affinity of the ligand. See e.g. Tucker, H. et al., J. Med. Chem., 1988, 31, 954-959.

Recently, AR modulating compounds having the anilide ring substituted with an alkyl group were described in WO 2005/000794. However, there is still need for AR modulating compounds which have optimal combination of properties such as high affinity and activity in androgen receptor, tissue-selective androgenic or anabolic effects, high oral bioavailability, low potential for drug-drug interactions, lack of serious adverse effects and a favourable metabolic profile.

SUMMARY OF THE INVENTION

It has now been found that the compound of formula (I) or an isomer, metabolite, or a pharmaceutically acceptable salt or ester thereof, has high affinity and activity in androgen receptor, provides tissue-selective androgenic or anabolic effects, good oral bioavailability and, at the same time, has low potential for drug-drug interactions, lacks serious adverse effects and has a favourable metabolic profile. Moreover, the compound of the present invention crystallizes easily and has little tendency to solvate formation. Therefore, the compound of the present invention is particularly useful as a tissue-selective androgen receptor modulator (SARM). The compound of the present invention is particularly suitable for use in hormonal therapy, especially in the treatment or prevention of AR dependent conditions, for example, but not limited to, in the treatment or prevention hypogonadism, muscle wasting, osteoporosis, benign prostate hyperplasia, obesity associated with a metabolic syndrome, male and female sexual dysfunction and reduced libido, and androgen decline in aging male or female. The beneficial androgenic or anabolic effects are obtained without concurrent harmful stimulation of the prostate.

The present invention provides a compound of formula (I)

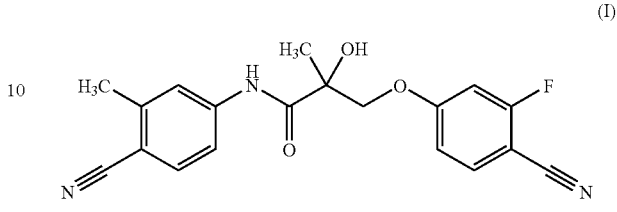

(I)

or an isomer, metabolite, or a pharmaceutically acceptable salt or ester thereof.

Particularly preferred compound of formula (I) is the S-enantiomer of the compound of formula (I), namely (2S)-3-(4-cyano-3-fluorophenoxy)-N-(4-cyano-3-methylphenyl)-2-hydroxy-2-methylpropionamide.

Particularly preferred metabolites of a compound of formula (I) are those which are useful in the treatment or prevention of androgen receptor (AR) dependent conditions. Such preferred metabolites include
2-cyano-5-[(S)-3-(4-cyano-3-fluorophenoxy)-2-hydroxy-2-methylpropionyl-amino]benzoic acid,
(S)-3-(4-cyano-3-fluorophenoxy)-N-(4-cyano-3-hydroxymethylphenyl)-2-hydroxy-2-methylpropionamide, and
(S)-3-(4-cyano-3-fluorophenoxy)-N-(4-cyano-3-formylphenyl)-2-hydroxy-2-methylpropionamide.

Pharmaceutically acceptable salts or esters of the above metabolites are also useful in the treatment or prevention of androgen receptor (AR) dependent conditions.

The present invention provides further a method of hormonal therapy, comprising administering to a subject in need thereof a therapeutically effective amount of a compound of formula (I) or its isomer, metabolite or a pharmaceutically acceptable salt or ester thereof.

The present invention provides further a method for the treatment or prevention of androgen receptor (AR) dependent conditions, comprising administering to a subject in need thereof a therapeutically effective amount of a compound of formula (I) or its isomer, metabolite or a pharmaceutically acceptable salt or ester thereof.

The present invention provides further a method the treatment or prevention of androgen deficiency, comprising administering to a subject in need thereof a therapeutically effective amount of a compound of formula (I) or its isomer, metabolite or a pharmaceutically acceptable salt or ester thereof.

The present invention also provides a pharmaceutical composition comprising a compound of formula (I) or its isomer, metabolite or a pharmaceutically acceptable salt or ester thereof, together with a pharmaceutically acceptable carrier.

DETAILED DESCRIPTION OF THE INVENTION

The compounds of the invention can be prepared by a variety of synthetic routes analogously to the methods known in the literature using suitable starting materials. In particular, the compounds of the invention can be prepared analogously to the general methods described in WO 2005/000794. For example, a compound of formula (I), including optically active enantiomers thereof, can be prepared according to the following reaction scheme, wherein R1 and R3 are methyl, R4 is hydrogen, R2 and R7 are cyano, R6 is fluoro, and R5, R8 and R9 are hydrogen:
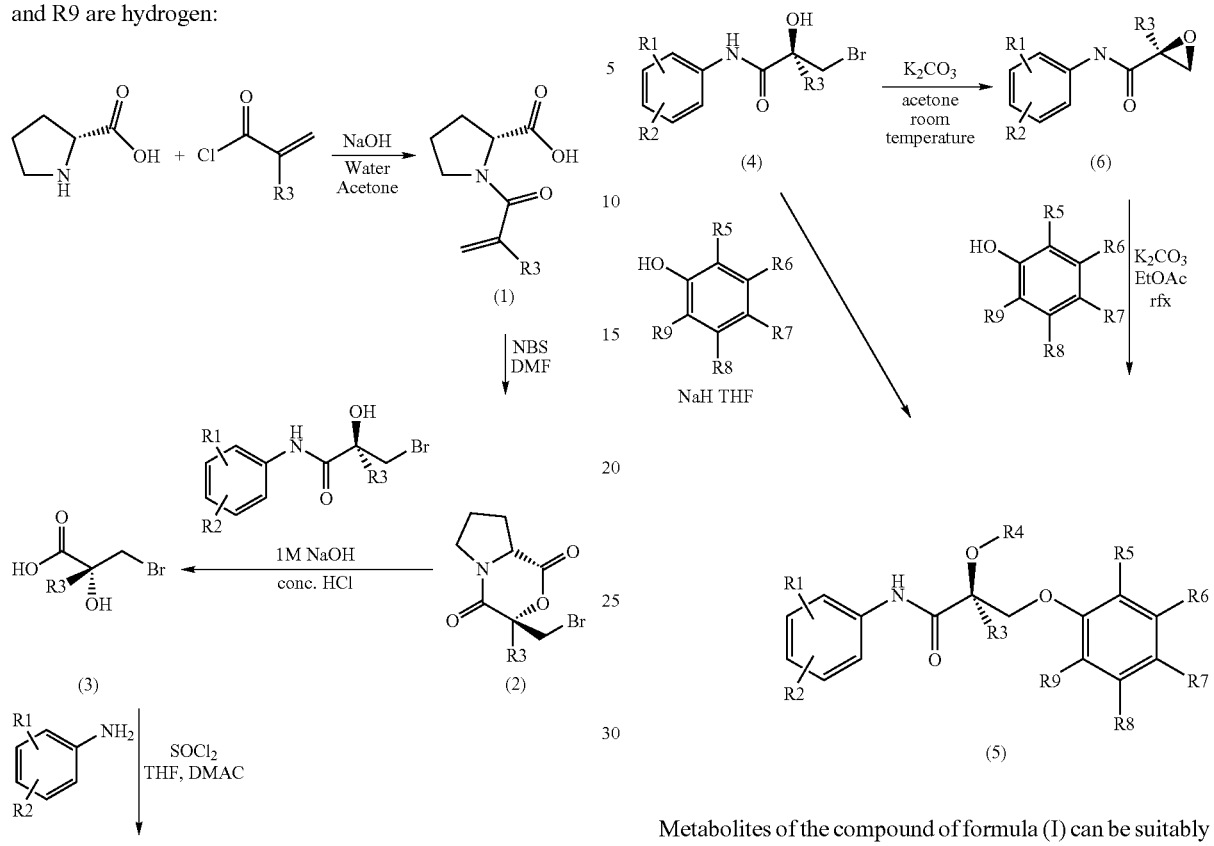
Metabolites of the compound of formula (I) can be suitably prepared e.g. according to the following reaction scheme:
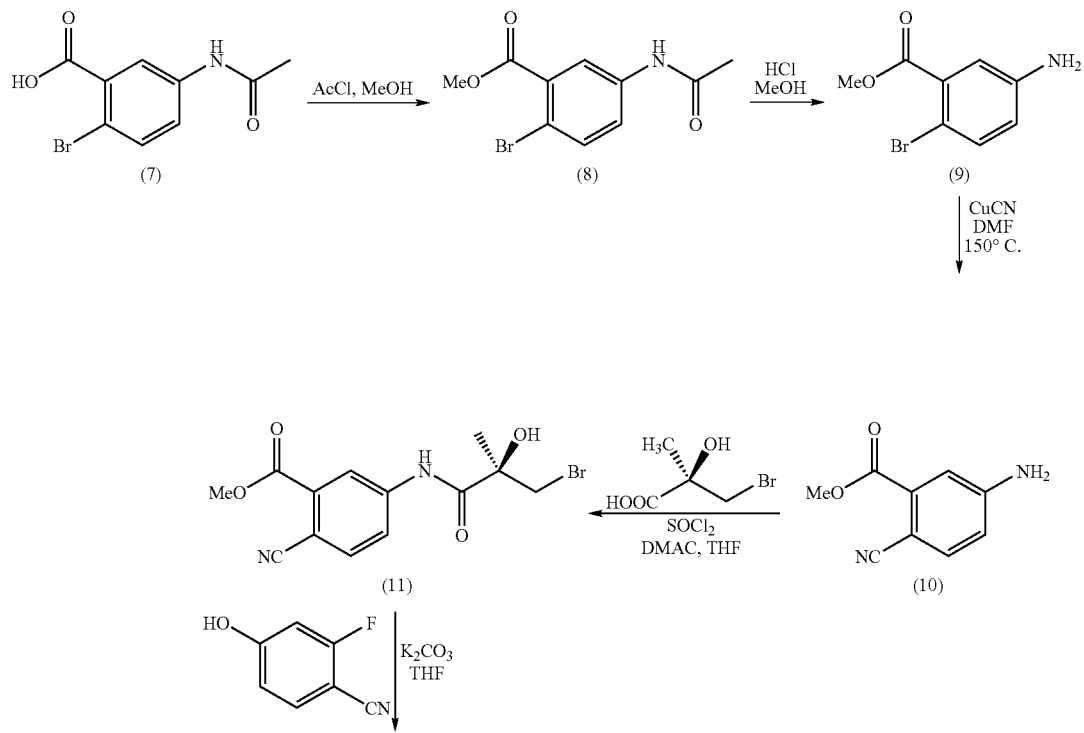

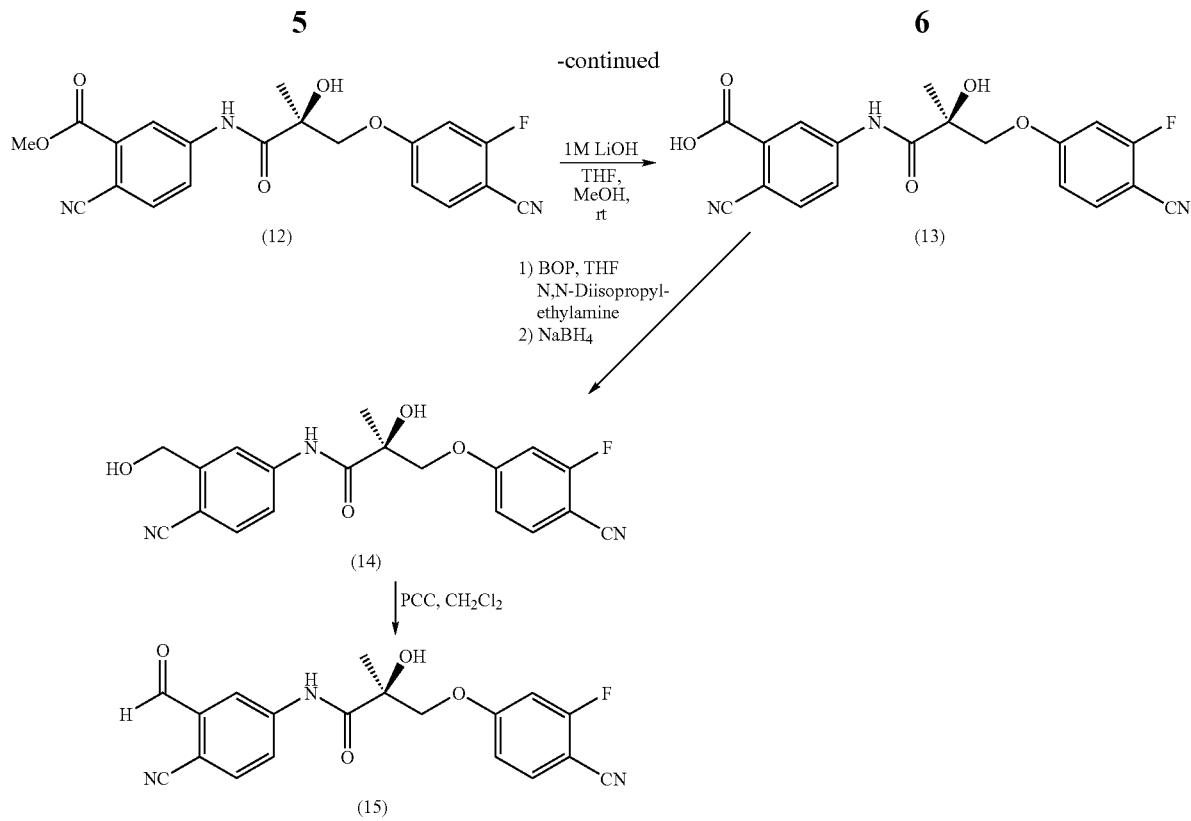

Pharmaceutically acceptable salts, e.g. acid addition salts with both organic and inorganic acids are well known in the field of pharmaceuticals. Non-limiting examples of these salts include chlorides, bromides, sulfates, nitrates, phosphates, sulfonates, formates, tartrates, maleates, citrates, benzoates, salicylates and ascorbates. Pharmaceutically acceptable esters, when applicable, may be prepared by known methods using pharmaceutically acceptable acids that are conventional in the field of pharmaceuticals and that retain the pharmacological properties of the free form. Non-limiting examples of these esters include esters of aliphatic or aromatic alcohols, e.g. methyl, ethyl, propyl, isopropyl, butyl, isobutyl, sec-butyl, tert-butyl esters. Phosphate esters and carbonate esters, are also within the scope of the invention.

The definition of formula (I) above is inclusive of all the possible stereo-isomers of the compounds, including geometric isomers, e.g. Z and E isomers (cis and trans isomers), and optical isomers, e.g. diastereomers and enantiomers, and all prodrug esters, e.g. phosphate esters and carbonate esters. Furthermore, the invention includes in its scope both the individual isomers and any mixtures thereof, e.g. racemic mixtures.

In one embodiment, the term "isomer" is meant to encompass optical isomers of the compounds of the invention. It will be appreciated by those skilled in the art that the compounds of the present invention contain at least one chiral center. Accordingly, the compounds of the invention may exist in optically active or racemic forms. It is to be understood that the present invention encompasses any racemic or optically active form, or mixtures thereof. In one embodiment, the compounds of the invention are the pure (R)-isomers. In another embodiment, the compounds of the invention are the pure (S)-isomers. In another embodiment, the compounds of the invention are a mixture of the (R) and the (S) isomers. In another embodiment, the compounds of the invention are a racemic mixture comprising an equal amount of the (R) and the (S) isomers. The individual isomers may be obtained using the corresponding isomeric forms of the starting material or they may be separated after the preparation of the end compound according to conventional separation methods. For the separation of optical isomers, e.g. enantiomers, from the mixture thereof the conventional resolution methods, e.g. fractional crystallisation, may be used.

As defined herein, the term "metabolite of a compound of formula (I)" means a biologically active agent which is formed in-vivo from a compound of formula (I).

According to the present invention, preferred are metabolites of a compound of formula (I) which are useful in the treatment or prevention of androgen receptor (AR) dependent conditions. Such preferred metabolites include
2-cyano-5-[(S)-3-(4-cyano-3-fluorophenoxy)-2-hydroxy-2-methylpropionyl-amino]benzoic acid,
(S)-3-(4-cyano-3-fluorophenoxy)-N-(4-cyano-3-hydroxymethylphenyl)-2-hydroxy-2-methylpropionamide, and
(S)-3-(4-cyano-3-fluorophenoxy)-N-(4-cyano-3-formylphenyl)-2-hydroxy-2-methylpropionamide.

Pharmaceutically acceptable salts or esters of the above metabolites are also useful in the treatment or prevention of androgen receptor (AR) dependent conditions.

For the treatment or prevention of androgen receptor (AR) dependent conditions a particularly preferred compound of formula (I) is the (S) isomer of the compound of formula (I), namely (2S)-3-(4-cyano-3-fluorophenoxy)-N-(4-cyano-3-methylphenyl)-2-hydroxy-2-methylpropionamide.

Compounds of the invention may be administered to a patient in therapeutically effective amounts which range usually from about 0.1 to about 1000 mg per day depending on the age, weight, ethnic group, condition of the patient, condition to be treated, administration route and the androgen (AR) modulator used. The compounds of the invention can be formulated into dosage forms using the principles known in the art. It can be given to a patient as such or in combination with suitable pharmaceutical excipients in the form of tablets, granules, capsules, suppositories, emulsions, suspensions or solutions. Choosing suitable ingredients for the composition is a routine for those of ordinary skill in the art. It is evident that suitable carriers, solvents, gel forming ingredients, dispersion forming ingredients, antioxidants, colours, sweeteners, wetting compounds and other ingredients normally used in this field of technology may be also used. The compositions containing the active compound can be given enterally or parenterally, the oral route being the preferred way. The contents of the active compound in the composition is from about 0.5 to 100%, preferably from about 0.5 to about 20%, per weight of the total composition.

The present invention will be explained in more detail by the following examples. The examples are meant only for illustrating purposes and do not limit the scope of the invention defined in claims.

EXAMPLES

Example 1 a) (2R)-3-Bromo-N-(4-cyano-3-methylphenyl)-2-hydroxy-2-methylpropion-amide

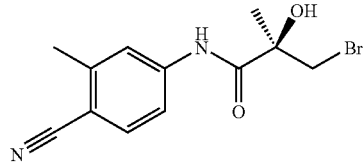 [SMILES: Cc1cc(NC(=O)[C@@](C)(O)CBr)ccc1C#N]

(2R)-3-Bromo-2-hydroxy-2-methylpropionic acid (1.52 g, 8.3 mmol) was dissolved in 35 ml of dry THF and 0.5 ml of dry DMA was added. Solution was cooled to 0° C. and thionyl chloride (0.8 ml; 10.8 mmol) was added dropwise. The solution was allowed to heat up to room temperature and stirred for 2 hours at room temperature. 4-Cyano-3-methylaniline (1.07 g, 8.1 mmol) was added in 5 ml of dry THF and reaction refluxed for 2 hours. THF was evaporated, the residue dissolved in 40 ml of $CH_2Cl_2$ and washed with 50 ml of 1% $NaHCO_3$ and then with 4×25 ml of water. The organic phase was evaporated and residue was dried under reduced pressure at 40° C. overnight to give 2.24 g of crude product which was crystallized from 5 ml of toluene (75° C. then cooled to room temperature and to 0° C.), filtered and washed with 5 ml of ice cold toluene. The precipitate was dried under reduced pressure overnight at 40° C. to give 1.54 g of the product.

$^1$H NMR (DMSO-$d_6$): 1.48 (3H, s), 2.45 (3H, s), 3.59 (1H, d, J=10.3 Hz), 3.83 (1H, d, J=10.3 Hz), 6.32 (1H, bs), 7.70 (1H, d, J=8.5 Hz), 7.78 (1H, dd, J=8.6 Hz, J=1.9 Hz), 7.92 (1H, d, J=1.4 Hz), 9.97 (1H, bs).

b) (2R)-2-Methyloxirane-2-carboxylicacid-(4-cyano-3-methylphenyl)amide

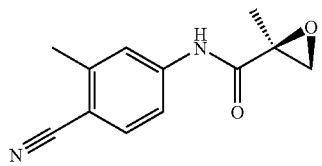

(2R)-3-Bromo-2-hydroxy-2-methyl-N-(4-cyano-3-methylphenyl)propion-amide (1.54 g, 5.2 mmol) was dissolved in 50 ml of toluene and stirred for 5 minutes with 15 ml of 1 M NaOH at room temperature. Organic layer was separated and washed with 2×25 ml of water. Toluene was filtered and evaporated to give 0.905 g of the product.

$^1$H NMR (DMSO-$d_6$): 1.54 (3H, s), 2.43 (3H, s), 2.99 (1H, d, J=5.1 Hz), 3.04 (1H, d, J=5.1 Hz), 7.65-7.75 (2H, m), 7.82 (1H, d, J=0.6 Hz), 9.77 (1H, bs).

c) (2S)-3-(4-Cyano-3-fluorophenoxy)-N-(4-cyano-3-methylphenyl)-2-hydroxy-2-methylpropionamide

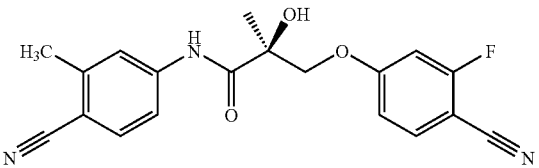 [SMILES: Cc1cc(NC(=O)[C@@](C)(O)COc2ccc(C#N)c(F)c2)ccc1C#N]

2-Fluoro-4-hydroxy benzonitrile (0.81 g, 5.9 mmol) and (2R)-2-methyl-oxirane-2-carboxylicacid-(4-cyano-3-methylphenyl)amide (0.905 g, 4.2 mmol) were dissolved in 17.6 ml of EtOAc. Anhydrous $K_2CO_3$ (0.29 g; 2.1 mmol) was added and the mixture heated to 50° C. and stirred for 25.5 hours. The mixture was cooled to room temperature, 30 ml of EtOAc added and washed first with 2×24 ml of 1M $Na_2CO_3$ and then 2×24 ml of water. Organic layer was dried over $Na_2SO_4$, filtered and evaporated to give 1.05 g of crude product.

$^1$H NMR (DMSO-$d_6$): 1.43 (3H, s), 2.44 (3H, s), 4.10 (1H, d, J=10.0 Hz), 4.36 (1H, d, J=10.0 Hz), 6.29 (1H, bs), 6.96 (1H, dd, J=8.8 Hz, J=2.3 Hz), 7.18 (1H, dd, J=11.9 Hz, J=2.3 Hz), 7.70 (1H, d, J=8.54 Hz), 7.76-7.83 (2H, m), 7.92 (1H, d, J=1.6 Hz), 10.05 (1H, bs).

Example 2 a) 5-Amino-2-bromobenzoic acid methyl ester

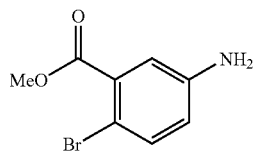 [SMILES: COC(=O)c1cc(N)ccc1Br]

Acetyl chloride (29.2 ml, 32.2 g, 410.7 mmol) was added dropwise to methanol (210 ml) at 0-10° C. under nitrogen atmosphere and the solution was stirred for 30 min at 0° C. After addition of 5-acetamido-2-bromobenzoic acid (21.2 g, 82.1 mmol) in methanol at 0° C. the solution was stirred for 3 h at 55° C. After evaporation of methanol ethyl acetate (160 ml) was added and stirring was continued for 1 h at room temperature. The precipitation was filtered off and it was dissolved in water. pH was adjusted to 8 with $NaHCO_3$. The mixture was extracted with ethyl acetate, washed with water, dried over $Na_2SO_4$ and concentrated under vacuum.

$^1$H NMR (400 MHz, DMSO-$d_6$): 3.38 (3H, s), 5.57 (2H, broad s), 6.64 (1H, dd, $^3$J=8.6 Hz, $^4$J=2.9 Hz), 6.95 (1H, d, $^4$J=2.8 Hz), 7.30 (1H, d, $^3$J=8.6 Hz).

b) 5-Amino-2-cyanobenzoic acid methyl ester

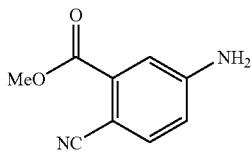

The mixture of 5-amino-2-bromobenzoic acid methyl ester (14.27 g, 62.0 mmol) and CuCN (6.11 g, 68.2 mmol) in DMF (130 ml) was heated at 150° C. for 1 h 10 min under nitrogen atmosphere. The mixture was cooled to 70° C. and poured into the mixture of water (250 ml) and 12.5% NH$_3$ (500 ml). The product was extracted into ethyl acetate (3×250 ml). The organic phase was washed several times with 12.5% NH$_3$ and water, dried over Na$_2$SO$_4$ and concentrated under vacuum.

$^1$H NMR (400 MHz, DMSO-d$_6$): 3.86 (3H, s), 6.46 (2H, broad s), 6.80 (1H, dd, $^3$J=8.5 Hz, J=2.4 Hz), 7.23 (1H, d, $^4$J=2.3 Hz), 7.51 (1H, d, 3J=8.5 Hz).

c) 5-((R)-3-Bromo-2-hydroxy-2-methylpropionylamino)-2-cyanobenzoic acid methyl ester

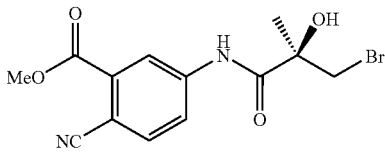

Thionyl chloride (3.9 ml, 5.3 mmol) was added dropwise to a solution of (2R)-3-bromo-2-hydroxy-2-methylpropionic acid (8.19 g, 44.8 mmol, prepared as described in WO 2005/000794) in 190 ml of THF and 5.8 ml of N,N-dimethylacetamide (DMAC) at 5° C. under nitrogen atmosphere. The solution was stirred for 3 h at room temperature. A solution of 5-amino-2-cyanobenzoic acid methyl ester (7.50 g, 4.3 mmol) in 75 ml of THF was added and the reaction mixture was maintained at 50° C. for 3 h and at room temperature for 16 h. The mixture was poured into water, extracted with ethyl acetate, washed with water, dried over Na$_2$SO$_4$ and evaporated under reduced pressure. The crude product was stirred in toluene and filtration afforded the purified compound.

$^1$H NMR (400 MHz, DMSO-d$_6$): 1.48 (3H, s), 3.58 (1H, d, $^2$J$_{gem}$=10.3 Hz), 3.82 (1H, d, $^2$J$_{gem}$=10.3 Hz), 3.92 (3sH, s), 6.35 (1H, s, —OH), 7.95 (1H, d, $^3$J=8.5 Hz), 8.16 (1H, dd, $^3$J=8.5 Hz, $^4$J=2.2 Hz), 8.73 (1H, d, $^4$J=2.2 Hz), 10.40 (1H, s, —NHCO—).

d) 2-Cyano-5-[(S)-3-(4-cyano-3-fluorophenoxy)-2-hydroxy-2-methyl-propionylamino]beizoic acid methyl ester

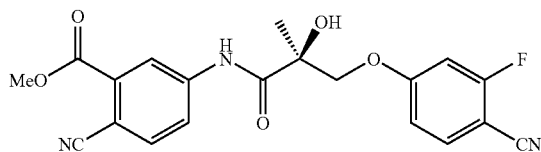

A mixture of 2-fluoro-4-hydroxybenzonitrile (4.80 g, 35.0 mmol), 5-((R)-3-Bromo-2-hydroxy-2-methylpropionylamino)-2-cyanobenzoic acid methyl ester (8.41 g, 24.7 mmol) and K$_2$CO$_3$ (8.51 g, 61.6 mmol) in THF (150 ml) was heated at 65° C. for 5 hours under nitrogen atmosphere. The mixture was cooled to room temperature and water was added. The product was extracted into ethyl acetate. The organic phase was washed with water, dried over Na$_2$SO$_4$ and evaporated. The crude product was purified by flash chromatography on silica gel (eluent: heptane/ethyl acetate 7:3-6:4).

$^1$H NMR (400 MHz, DMSO-d$_6$): 1.44 (3H, s), 3.91 (3H, s), 4.12 (1H, d, $^2$J$_{gem}$=0.1 Hz), 4.38 (1H, d, $^2$J$_{gem}$=10.1 Hz), 6.33 (1H, s, —OH), 6.96 (1H, dd, $^3$J$_{H,H}$=8.8Hz, $^4$J$_{H,H}$=2.3Hz), 7.19 (1H, dd, $^3$J$_{H,F}$=11.9Hz, $^4$J$_{H,H}$=2.3 Hz), 7.80 (1H, t, $^3$J$_{H,H}$=$^4$J$_{H,F}$=8.4 Hz), 7.95 (1H, d, $^3$J=8.5 Hz), 8.17 (1H, dd, $^3$J=8.5 Hz, $^4$J=2.2 Hz), 8.73 (1H, d, $^4$J=2.1 Hz), 10.47 (1H, s, —NHCO—).

e) 2-Cyano-5-[(S)-3-(4-cyano-3-fluorophenoxy)-2-hydroxy-2-methyl-propionylamino]benzoic acid

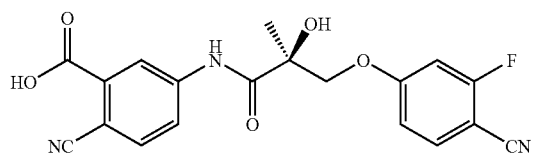

1 M LiOH (34 ml) was added to a solution of 2-cyano-5-[(S)-3-(4-cyano-3-fluorophenoxy)-2-hydroxy-2-methylpropionylamino]benzoic acid methyl ester (4.52 g, 11.4 mmol) in THF (50 ml) and methanol (6 ml) at 16-18° C. The resulting solution was stirred at room temperature for 2.5 h. The solvents were evaporated and pH was adjusted to 2 with HCl solution. The product was extracted into ethyl acetate. The organic phase was washed with water, dried over Na$_2$SO$_4$ and evaporated. The residue was purified by flash chromatography (eluent: CH$_2$Cl$_2$/MeOH 98:2). Trituration in hot CH$_2$Cl$_2$, cooling to room temperature and filtration yielded the title compound.

$^1$H NMR (400 MHz, DMSO-d$_6$): 1.44 (3H, s), 4.11 (1H, d, $^2$J$_{gem}$=10.1 Hz), 4.37 (1H, d, $^2$J$_{gem}$=10.1 Hz), 6.32 (1H, s, —OH), 6.96 (1H, dd, $^3$J$_{H,H}$=8.8 Hz, $^4$J$_{H,H}$=2.4 Hz), 7.20 (1H, dd, $^3$J$_{H,F}$=11.9 Hz, $^4$J$_{H,H}$=2.3 Hz), 7.80 (1H, t, $^3$J$_{H,H}$=$^4$J$_{H,F}$=8.4 Hz), 7.91 (1H, d, $^3$J=8.5 Hz), 8.14 (1H, dd, $^3$J=8.5 Hz, $^4$J=2.2 Hz), 8.67 (1H, d, $^4$J=2.1 Hz), 10.41 (1H, s, —NHCO—), 13.84 (1H, broad s, COOH).

f) (S)-3-(4-Cyano-3-fluorophenoxy)-N-(4-cyano-3-hydroxymethylphenyl)-2-hydroxy-2-methylpropionamide

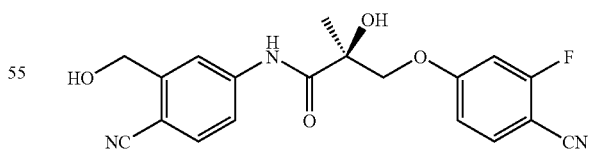

(Benzotriazol-1-yloxy)tris(dimethylamino)phosphonium hexaflurophosphate (BOP, 335 mg, 0.757 mmol) was added to a solution of 2-cyano-5-[(S)-3-(4-cyano-3-fluorophenoxy)-2-hydroxy-2-metlhylpropioniylamino]benzoic acid (250 mg, 0.652 mmol) in anhydrous THF (8 ml) under nitrogen. N,N-diisopropylethylamine (0.14 ml, 0.803 mmol) was added to a mixture and it was stirred at room temperature for 10 min. Then NaBH$_4$ (30 mg, 0.793 mmol) was added, and the mixture was stirred at room temperature for 50 min. The solvent was removed under reduced pressure, and the residue was dissolved into ethyl acetate. The organic phase was washed with 0.5 M HCl, concentrated $NaHCO_3$ and brine and dried over $Na_2SO_4$. The solvent was removed under reduced pressure, and the residue was purified by flash chromatography on siliga gel using dichloromethane/methanol (95:5) as the eluent to provide the desired alcohol.

$^1$H NMR (400 MHz, DMSO-$d_6$): 1.42 (3H, s), 4.09 (1H, d, $^2J_{gem}$=10.0 Hz), 4.35 (1H, d, $^2J_{gem}$=10.1 Hz), 4.59 (2H, d, J=5.6Hz), 5.52 (1H, t, $^3$J=5.5 Hz, —CH$_2$OH), 6.23 (1H, s, —OH), 6.94 (1H, d, $^3J_{H,H}$=8.8 Hz, $^4J_{H,H}$=2.3 Hz), 7.16 (1H, dd, $^3J_{H,F}$=11.9 Hz, $^4J_{H,H}$=2.3 Hz), 7.70 (1H, d, $^3$J=8.4 Hz), 7.78 (2H, m), 8.14 (1H, d, $^4$J=1.5 Hz), 10.09 (1H, s, —NHCO—).

g) (S)-3-(4-Cyano-3-fluorophenoxy)-N-(4-cyano-3-formylphenyl)-2-hydroxy-2-methylpropionamide

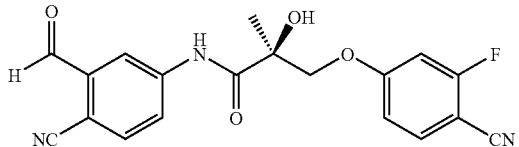

(S)-3-(4-Cyano-3-fluorophenoxy)-N-(4-cyano-3-hydroxymethylphenyl)-2-hydroxy-2-methylpropionamide (170 mg, 0.460 mmol) and pyridinium chloro-chromate (150 mg, 0.696 mmol) in anhydrous $CH_2Cl_2$ (10 ml) were stirred for 1 h 45 min at room temperature. Then the solvent was evaporated and the residue was purified by flash chromatography on silica gel ($CH_2Cl_2$/MeOH 96:4) to afford (S)-3-(4-Cyano-3-fluorophenoxy)-N-(4-cyano-3-formylphenyl)-2-hydroxy-2-methyl-propionamide.

$^1$H NMR (400 MHz, DMSO-$d_6$): 1.44 (3H, s), 4.11 (1H, d, $^2J_{gem}$=10.1 Hz), 4.37 (1H, d, $^2J_{gem}$=10.0 Hz), 6.32 (1H, broad s, —OH), 6.94 (1H, dd, $^3J_{H,H}$=8.8 Hz, $^4J_{H,H}$=2.2 Hz), 7.16 (1H, dd, $^3J_{H,F}$=11.9Hz, $J_{H,H}$=2.3 Hz), 7.78 (1H, t, $^3J_{H,H}$=$^4J_{H,F}$=8.3 Hz), 7.97 (1H, d, $^3$J=8.5 Hz), 8.18 (1H, dd, $^3$J=8.5 Hz, $^4$J=2.2 Hz), 8.61 (1H, d, $^4$J=1.9 Hz), 10.05 (1H, d, 4J=0.4 Hz, —CHO), 10.46 (1H, broad s, —NHCO—).

The invention claimed is:

1. A compound of formula (I)

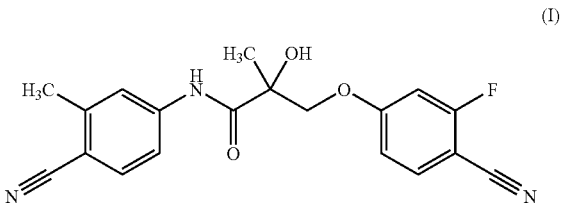 [SMILES: Cc1cc(NC(=O)C(C)(O)COc2ccc(C#N)c(F)c2)ccc1C#N]

or an optical isomer, metabolite,
which is 2-cyano-5-[(S)-3-(4-cyano-3-fluorophenoxy)-2-hydroxy-2-methylpropionylamino]benzoic acid, (S)-3-(4-cyano-3-fluorophenoxy)-N-(4-cyano-3-hydroxymethylphenyl)-2-hydroxy-2-methylpropionamide or (S)-3-(4-cyano-3-fluorophenoxy)-N-(4-cyano-3-formylphenyl)-2-hydroxy-2-methylpropionamide,
or a pharmaceutically acceptable salt thereof.

2. The compound according to claim 1 of formula (I), which is (2S)-3-(4-cyano-3-fluoro-phenoxy)-N-(4-cyano-3-methylphenyl)-2-hydroxy-2-methylpropionamide.

3. The pharmaceutical composition comprising a compound according to claim 1 and a pharmaceutically acceptable carrier.

4. The method for the treatment of androgen deficiency, comprising administering to a subject in need thereof a therapeutically effective amount of a compound according to claim 1.

5. A pharmaceutical composition comprising (2S)-3-(4-cyano-3-fluoro-phenoxy)-N-(4-cyano-3-methylphenyl)-2-hydroxy-2-methylpropionamide and a pharmaceutically acceptable carrier.

6. A method for the treatment of androgen deficiency, comprising administering to a subject in need thereof a therapeutically effective amount of (2S)-3-(4-cyano-3-fluoro-phenoxy)-N-(4-cyano-3-methylphenyl)-2-hydroxy-2-methyl-propionamide.

* * * * *